(12) United States Patent
Yan et al.

(10) Patent No.: US 11,135,450 B2
(45) Date of Patent: Oct. 5, 2021

(54) RADIATION THERAPY APPARATUS AND BEAM IMAGING METHOD

(71) Applicants: Shenzhen OUR New Medical Technologies Development Co., Ltd., Guangdong (CN); OUR UNITED CORPORATION, Shaanxi (CN)

(72) Inventors: Hao Yan, Guangdong (CN); Jinsheng Li, Guangdong (CN)

(73) Assignees: SHENZHEN OUR NEW MEDICAL TECHNOLOGIES DEVELOPMENT CO., LTD.; OUR UNITED CORPORATION

( * ) Notice: Subject to any disclaimer, the term of this patent is extended or adjusted under 35 U.S.C. 154(b) by 275 days.

(21) Appl. No.: 16/264,811

(22) Filed: Feb. 1, 2019

(65) Prior Publication Data

US 2019/0175945 A1    Jun. 13, 2019

Related U.S. Application Data

(63) Continuation of application No. PCT/CN2016/092740, filed on Aug. 1, 2016.

(51) Int. Cl.
*A61N 5/10* (2006.01)

(52) U.S. Cl.
CPC ........... *A61N 5/1067* (2013.01); *A61N 5/107* (2013.01); *A61N 5/1049* (2013.01);
(Continued)

(58) Field of Classification Search
CPC .... A61N 2005/1019; A61N 2005/1054; A61N 2005/1061; A61N 5/1031; A61N 5/1049;
(Continued)

(56) References Cited

U.S. PATENT DOCUMENTS

| 6,501,828 B1 | 12/2002 | Popescu ........................ 378/150 |
| 6,914,959 B2 | 7/2005 | Bailey et al. ................... 378/65 |

(Continued)

FOREIGN PATENT DOCUMENTS

| CN | 1853566 A | 11/2006 |
| CN | 1919374 A | 2/2007 |

(Continued)

OTHER PUBLICATIONS

Chinese Office Action, dated Nov. 2, 2018, issued in corresponding Chinese Patent Application No. 201680002219.2. English translation. Total 29 pages.
(Continued)

*Primary Examiner* — Irakli Kiknadze
(74) *Attorney, Agent, or Firm* — Ostrolenk Faber LLP

(57) ABSTRACT

The present disclosure falls into the field of medical apparatus, and discloses a radiation therapy apparatus and a beam imaging method, wherein the radiation therapy apparatus includes: a treatment head including multiple radiation sources distributed on one side of a target region, radiation beams emitted by the multiple radiation sources intersecting in the target region, and a lesion being located within the target region; a beam detector used for receiving a radiation beams passing through the lesion and emitted by the radiation sources to acquire projection data of each radiation beam passing through the lesion, and generating a slice image of the lesion according to the acquired projection data; and a processor used for constructing an image of the lesion in the target region based on the slice image generated by the beam detector. The radiation therapy apparatus of the present disclosure can implement a three-dimensional imaging process in real time, the treatment head of the beam therapy apparatus can be directly used for tracking tumors,
(Continued)

and the human body can be positioned according to the reconstructed three-dimensional image before surgery.

13 Claims, 9 Drawing Sheets

(52) U.S. Cl.
CPC .......... *A61N 5/1084* (2013.01); *A61N 5/1031* (2013.01); *A61N 2005/1019* (2013.01); *A61N 2005/1054* (2013.01); *A61N 2005/1061* (2013.01)

(58) Field of Classification Search
CPC .... A61N 5/1067; A61N 5/107; A61N 5/1084; A61N 5/1082; A61N 2005/1062; A61N 5/1037; A61N 5/1042; A61N 5/10; A61N 5/1047; A61N 5/1081; A61N 5/1039; A61N 5/1045; A61N 5/103; A61N 5/1036; A61N 5/1077; A61N 2005/1032; A61N 5/1068; A61N 2005/1085; A61N 2005/1091; A61N 2005/1095; A61N 5/1071; A61N 5/1048; A61N 2005/1087; A61N 2005/105; A61N 5/1043; A61N 2005/1059; A61N 2005/1055; A61N 2005/1052; A61N 2005/1058; A61N 2005/1076; A61N 5/1075; A61B 6/032; A61B 6/025; A61B 6/4085; A61B 6/482; A61B 6/502; A61B 6/4441; A61B 5/0036; A61B 6/4014; A61B 6/0414; A61B 2034/101; A61B 34/10; A61B 5/08; A61B 5/113; A61B 5/4836; A61B 6/027; A61B 6/06; A61B 6/4452; A61B 5/055; A61B 6/0487; A61B 6/4435; A61B 6/405; A61B 6/5205; A61B 6/4241; A61B 6/5241; A61B 5/004; A61B 5/0095; A61B 6/488; A61B 6/544; A61B 6/0407; A61B 6/00; A61B 6/12; A61B 6/4007; A61B 6/4429; A61B 6/461; A61B 6/486; A61B 6/54; A61B 8/13; A61B 6/03; A61B 6/035; A61B 6/08; A61B 5/0071; A61B 5/0075; A61B 5/418; A61B 5/4312; A61B 5/1127; A61B 5/087; A61B 5/1114; A61B 5/1135; A61B 5/704; A61B 6/037; A61B 6/4258; A61B 6/4417; A61B 6/4458; A61B 6/481; A61B 6/508; A61B 6/5217; A61B 6/5235; A61B 2090/374; G01N 2223/419; G01N 23/046; G01N 2223/308; G01N 23/044; G01N 2223/612; G01N 2223/204; G01N 2223/313; G01N 2223/33; G01N 2223/501; G01N 23/02; G01N 23/04; G01N 2223/423; G06T 11/06; G06T 2207/10112; G06T 11/005; G06T 11/008; G06T 2207/30004; G06T 2211/408; G06T 2211/412; G06T 2211/424; G06T 2211/436; G06T 7/0012; G06T 7/246; G06T 15/08; G06T 2200/04; G06T 2207/10048; G06T 2207/10076; G06T 2207/10081; G06T 2207/10101; G06T 2207/30068; G06T 5/00; G06T 2207/20224; G06T 11/003; G06T 5/002; G06T 5/50; G06T 11/006; G06T 2210/41; G06T 2211/404; G06T 2211/428; G06T 2211/432; G06T 7/30; G06T 1/161; G06T 1/17; G06T 7/00; G06T 2207/10072; G06T 2207/20044; G06T 2207/30061; G06T 2207/30101; G06T 2207/30172; G06T 7/11; G06T 7/64; G06T 2207/10056; G06T 2207/20076; G06T 2207/20081; G06T 2207/10121; G06T 2207/10124; G06T 2207/30048; G06T 7/33; G21K 1/093; G21K 1/02; G21K 1/025; G21K 1/046; G21K 1/10; G21K 5/04; G21K 1/04; G21K 1/06; G21K 2201/061; G21K 5/10; G01T 1/1611; G01T 1/29; G01T 1/2928; G01T 1/241; G01T 1/02; G01T 1/161; G01T 1/17; G01T 7/00; G01T 1/1642; G01T 1/249; G06K 9/78; G06K 9/46; H01J 2235/062; H01J 2235/068; H01J 35/00; H01J 35/02; H01J 35/16; H01J 35/32; H01J 2201/304; H01J 2201/342; H01J 35/06; H01J 35/066; H01J 35/30; H05G 1/70; H05G 1/04; H04N 19/103; H04N 19/14; H04N 19/162; H04N 19/17; H04N 19/174; H04N 19/593
USPC .......................... 378/4, 9, 11, 12, 64, 62, 65
See application file for complete search history.

(56) References Cited

U.S. PATENT DOCUMENTS

| | | | |
|---|---|---|---|
| 7,711,169 B2* | 5/2010 | West | A61N 5/103 382/128 |
| 7,936,858 B2 | 5/2011 | Hashemi | 378/22 |
| 8,559,596 B2* | 10/2013 | Thomson | A61N 5/1067 378/65 |
| 2004/0264626 A1 | 12/2004 | Besson | 378/4 |
| 2006/0245537 A1 | 11/2006 | Bakai et al. | 378/9 |
| 2007/0036265 A1* | 2/2007 | Jing | A61B 6/4028 378/37 |
| 2008/0212737 A1* | 9/2008 | D'Souza | A61N 5/1049 378/65 |
| 2009/0086889 A1 | 4/2009 | Hashemi | 378/22 |
| 2009/0180589 A1* | 7/2009 | Wang | A61N 5/1082 378/65 |
| 2010/0232565 A1 | 9/2010 | Ye et al. | 378/5 |
| 2012/0177171 A1 | 7/2012 | Gutfleisch et al. | 378/4 |
| 2012/0330154 A1 | 12/2012 | Beasley et al. | 600/436 |
| 2016/0074673 A1 | 3/2016 | Allen et al. | |
| 2019/0126070 A1* | 5/2019 | Hsieh | G06T 11/006 |

FOREIGN PATENT DOCUMENTS

| | | |
|---|---|---|
| CN | 101505658 A | 8/2009 |
| CN | 101808582 A | 8/2010 |
| CN | 102415897 A | 4/2012 |
| CN | 102781313 A | 11/2012 |
| CN | 103386168 A | 11/2013 |
| CN | 103845816 A | 6/2014 |
| CN | 104921745 A | 9/2015 |
| CN | 105413067 A | 3/2016 |
| CN | 205411197 U | 8/2016 |
| DE | 199 50 794 A1 | 6/2001 |

OTHER PUBLICATIONS

Chinese Office Action, dated Apr. 16, 2019, issued in corresponding Chinese Patent Application No. 201680002219.2. English translation. Total 32 pages.
International Search Report dated Jan. 26, 2017 in corresponding PCT International Application No. PCT/CN2016/092740.

(56) References Cited

OTHER PUBLICATIONS

Written Opinion dated Jan. 26, 2017 in corresponding PCT International Application No. PCT/CN2016/092740.

* cited by examiner

RADIATION THERAPY APPARATUS AND BEAM IMAGING METHOD

This application is a Bypass Continuation Application of PCT/CN2016/092740 filed Aug. 1, 2016, titled "RADIATION THERAPY APPARATUS AND BEAM IMAGING METHOD", the entirety is incorporated herein by reference.

TECHNICAL FIELD

The present disclosure relates to the field of medical apparatus, more particularly, to a radiation therapy apparatus and a beam imaging method.

BACKGROUND

A beam therapy apparatus is used to treat a tumor. Typically, the beam therapy apparatus includes a beam treatment head, a bed, and a control system. The beam treatment head includes a radiation source device, a driving device, etc. The radiation source device is provided with multiple radiation sources arranged spherically or arranged into a camber. These radiation sources are divided into multiple groups, and during the treatment, the radiation sources are turned on by controlling the collimating apertures on the beam treatment table, so as to emit beams. The function of the bed is to place the patient at a proper position so that the beam can accurately irradiate the tumor.

When the patient is placed, in vivo imaging of the patient shall be performed using an X-ray light source. Then the tumor is positioned according to the imaging result, and thereby the patient is placed according to the imaging result. Therefore, the existing beam therapy apparatus needs to be configured with a X-ray image processing system, wherein the X-ray image processing system includes a light source generating device and corresponding accessories such as a high voltage generator, a cable, and an electronic control component. This entails a high cost of the device.

SUMMARY

The present disclosure provided a radiation therapy apparatus and a beam imaging method. The treatment head contained in the radiation therapy apparatus is a multi-source focused treatment head. In the beam imaging method, radiation beams of the multi-source focused treatment head may be utilized to image the lesion, thereby eliminating the need to configure an X-ray image processing system.

The object of the present disclosure is achieved by the following technical solution:

A radiation therapy apparatus, comprising:

a treatment head, wherein the treatment head comprises multiple radiation sources distributed on a side of a target region, radiation beams emitted by at least two radiation sources intersect in the target region; a lesion is located in the target region;

a beam detector for receiving a radiation beam passing through the lesion and emitted by at least one radiation source to acquire projection data of the radiation beam passing through the lesion, and generating a slice image of the lesion according to the acquired projection data; and a processor, configured to construct an image of the lesion in the target region according to the slice image generated by the beam detector.

Exemplarily, the radiation therapy apparatus further includes a first driving mechanism for driving the treatment head to rotate circumferentially.

Exemplarily, the radiation therapy apparatus further includes a pivoting mechanism for driving the treatment head to pivot about an axis.

Exemplarily, the radiation therapy apparatus further includes a bed and a second driving mechanism;

the processor is further configured to determine a position of the lesion according to the image of the lesion; the second driving mechanism is configured to drive the bed to move according to a position of the lesion determined by the processor.

Exemplarily, the treatment head periodically receives a radiation beam according to a preset time or continuously receives a radiation beam;

The processor is further configured to acquire a reference position of the lesion, wherein the reference position of the lesion is a position of the lesion in the treatment plan, or a position of the lesion determined according to the radiation beam emitted by the treatment head previous time;

the processor is further configured to compare the acquired reference position of the lesion with the determined position of the lesion;

the second driving mechanism is further configured to drive the bed to move according to the comparison result determined by the processor.

Exemplarily, processor is further configured to determine the position of the lesion according to the image of the lesion;

the radiation therapy apparatus further includes a third driving mechanism configured to drive the treatment head to move, thereby adjusting the position of the target.

Exemplarily, the beam detector periodically receives a radiation beam according to a preset time;

the processor is further configured to acquire a reference position of the lesion, wherein the reference position of the lesion is a position of the lesion in the treatment plan, or a position of the lesion determined according to the radiation beam emitted by the treatment head previous time;

the processor is further configured to compare the acquired reference position of the lesion with the determined position of the lesion;

the third driving mechanism is further configured to drive the bed to move according to the comparison result determined by the processor.

Exemplarily, the processor is further configured to acquire a motion signal of the human body, and determine a weight of the comparison result and a weight of the motion signal of the human body;

in a case where the weight of the motion signal of the human body is less than the weight of the comparison result, the second driving mechanism is further configured to drive the bed and/or the treatment head to move according to the motion signal of the human body;

in a case where the weight of the motion signal of the human body is greater than the weight of the comparison result, the second driving mechanism is further configured to drive the bed and/or the treatment head to move according to the comparison result;

Exemplarily, the beam detector periodically receives a radiation beam according to a preset time;

the processor is further configured to acquire a reference position of the lesion and compare the acquired reference position of the lesion with the determined position of the lesion; the reference position of the lesion is a position of the lesion in the treatment plan, or a position of the lesion determined according to the radiation beam emitted by the treatment head previous time;

the treatment head is further configured to adjust the beam intensity according to the comparison result of the processor.

Exemplarily, the processor is further configured to acquire a motion signal of the human body, and determine a weight of the comparison result and a weight of the motion signal of the human body;

in a case where the weight of the motion signal of the human body is less than the weight of the comparison result, the treatment head is further configured to adjust the beam intensity according to the motion signal of the human body;

in a case where the weight of the motion signal of the human body is greater than the weight of the comparison result, the treatment head is further configured to adjust the beam intensity according to the comparison result.

A beam imaging method applied to the radiation therapy apparatus, the radiation therapy apparatus comprising a treatment head and a beam detector, wherein the treatment head comprises multiple radiation sources distributed on one side of the target region, multiple radiation beams emitted by at least two radiation sources intersect in the target region; the imaging method comprises:

emitting, by at least one of the radiation sources;

acquiring first slice projection data of target region according to the radiation beam passing through the lesion received by the beam detector; the first slice projection data including lesion image information when the treatment head is at a first position;

constructing an image of the lesion in the target region based on the first slice projection data.

Exemplarily, the method further comprises: rotating the treatment head to a second position at a preset angle, emitting, by at least one of the radiation sources, a radiation beam at the second position;

acquiring a second slice projection data of target region according to the radiation beam passing through the target region received by the detector, wherein the second slice projection data includes lesion image information when the treatment head is at the second position;

constructing an image of the lesion in the target region according to the second slice projection data or according to the first slice projection data and the second slice projection data.

Exemplarily, the preset angle is 90°.

Exemplarily, the radiation therapy apparatus further includes a bed. The method further includes: moving the bed to adjust a distance between the bed and the treatment head.

Exemplarily, the method further includes determining a position of the lesion according to the image, and adjusting the position of the lesion in the target region and/or the position of the target according to the position of the lesion in the image such that the lesion in the target region is located in the target.

Exemplarily, the radiation therapy apparatus further includes a bed, the method further comprises:

acquiring a reference position of the lesion, wherein the reference position of the lesion is a position of the lesion in the treatment plan, or a position of the lesion determined according to the radiation beam emitted by the treatment head previous time;

comparing the reference position of the lesion with the position of the lesion determined according to the image;

adjusting the position of the bed and/or the position of target according to the comparison result such that the lesion of the target region is located in the target, and/or adjusting the beam intensity such that the lesion is irradiated by a first dose of beam at the target position, is irradiated by a second dose of beam or is not irradiated at all at the non-target position, wherein the first dose is greater than the second dose.

Exemplarily, before the position of the bed is adjusted according to the comparison result and/or the beam intensity is adjusted, the method further includes:

acquiring a motion signal of the human body;

determining a weight of the motion signal of the human body and a weight of the comparison result;

adjusting the position of the bed and/or the position of the target according to the comparison result, and/or adjusting the beam intensity in a case where the weight of the motion signal of the human body is less than the weight of the comparison result; adjusting the position of the bed according to the motion signal, and/or, adjusting the beam intensity in a case where the weight of the motion signal of the human body is greater than the weight of the comparison result.

Exemplarily, the first driving mechanism is further configured to drive the treatment head to move, such that the treatment head can emit radiation beams at different locations;

the beam detector can also be configured to receive a radiation beam emitted by a radiation source at different locations of the treatment head to obtain a slice image of the same radiation source at different locations;

the processor is further configured to create an image of the target region according to the slice images at different locations;

Exemplarily, at least two of the multiple radiation sources simultaneously emit a beam or sequentially emit a beam.

Exemplarily, among the multiple radiation sources, any two of the radiation sources have a preset angle.

Exemplarily, the treatment head includes at least two radiation sources in a circumferential direction.

Exemplarily, at least two of the multiple radiation sources simultaneously emit a beam or sequentially emit a beam.

Exemplarily, the first slice projection data includes sub-slice projection data corresponding to each of the radiation sources;

the method of establishing an image of the target region according to the first slice projection data specifically includes:

establish an image of the target region according to projection data of each sub-slice corresponding to the at least two radiation sources.

Exemplarily, the at least two radiation sources simultaneously emit a beam or sequentially emit a beam.

In the radiation therapy apparatus of the present disclosure, the multiple radiation sources on the treatment head are distributed on a side of the target region at a preset angle. The radiation beams emitted by the multiple radiation sources intersect. When the multiple radiation sources simultaneously emit radiation beams from different angles and pass through the lesion located in the target region, a slice image of the lesion may be generated by the beam detector. The processor may generate a three-dimensional image of the lesion according to the slice image. Since multiple radiation sources irradiate from multiple angles in one irradiation, multiple projection data can be obtained in one process. Thus, the radiation therapy apparatus of the present disclosure can implement a three-dimensional imaging process in real time, so that the tumor can be tracked in real time without using an X-ray imaging system in a beam therapy operation, and the tumor can be directly tracked by the treatment head of the beam therapy apparatus. Furthermore, the human body may be placed properly before surgery by virtue of a reconstructed three-dimensional image of the lesion after the beam of the treatment head penetrates the human body.

DETAILED DESCRIPTION

The present disclosure will now be further described with reference to the drawings and preferred embodiments.

Example 1

Figure 1:
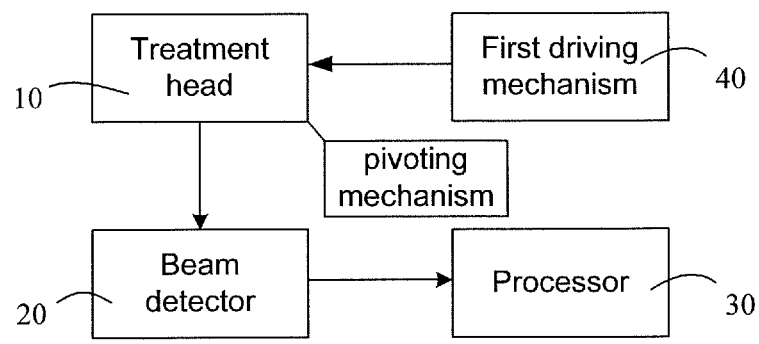
FIG. 1 is a schematic structural diagram of a radiation therapy apparatus according to example 1 of the present disclosure.

As shown in FIG. 1, the present embodiment provides a radiation therapy apparatus. The apparatus includes a treatment head 10, a beam detector 20, and a processor 30. The treatment head 10 is provided with multiple radiation sources, wherein the multiple radiation sources are distributed on a side of the target region, and radiation beams (at least two radiation beams) emitted by the multiple radiation sources intersect, wherein a lesion is disposed in the target region to receive radiation beams.

Figure 4:
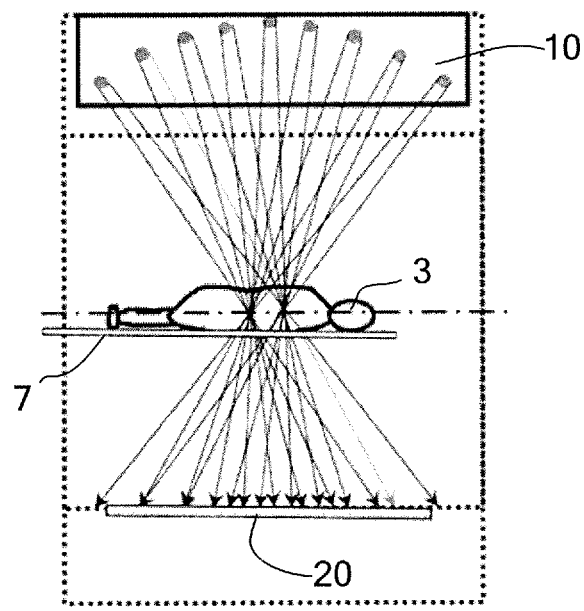
FIG. 4 is a schematic diagram of an irradiation process of a beam therapy apparatus according to embodiments of the present disclosure.

Generally, the radiation source on the treatment head may be a source of radiation such as a cobalt source or an accelerator source that emits a radiation beam and can penetrate the human body. The embodiment of the present application exemplifies taking a radiation source as a cobalt source as an example. In the present embodiment, the treatment head 10 is mainly used to bear a radiation source, and has the function of turning on and shielding the radiation source. The treatment head 10 turns on and shields the radiation source may through a collimator disposed thereon. The multiple radiation sources on the treatment head 10 are disposed on a side of the target region, the target region is an area where the human lesion is located and through which the radiation beam of the radiation source passes, wherein the position of the human lesion is a part of the human body where the lesion which is tumor occurs. As shown in FIG. 4, the radiation sources may be arranged in the treatment head 10 in a shape of a spherical plane, and the beams emitted from the radiation sources pass through the target region and the position of the lesion of the human body from one side. Merely one of the multiple radiation sources on the treatment head 10 may be turned on, that is, one radiation source emits a radiation beam and passes through the lesion. Of course, multiple or all of the radiation sources can be simultaneously turned on, so that the radiation beams emitted by the radiation sources can pass through the lesion. The multiple radiation sources may simultaneously emit a beam or sequentially emit a beam. If more radiation beams pass through the lesion of the human body, more data about the lesion will be obtained. Of course, in practical applications, it is necessary to select an appropriate number of radiation sources depending on the size of the lesion.

Figure 3:
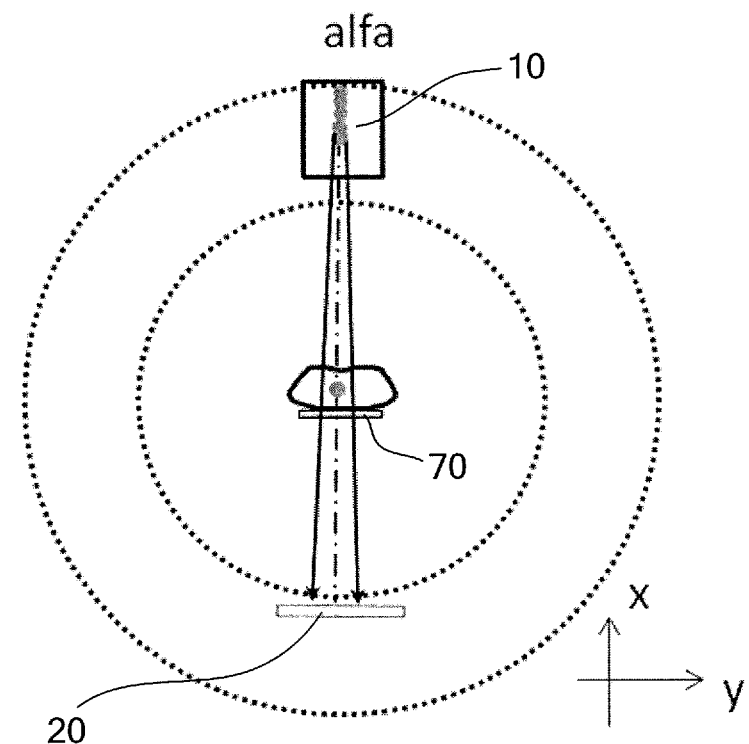
FIG. 3 is a schematic diagram illustrating that a radiation source according to embodiments of the present disclosure emits a beam at an incident angle of alfa.

In another embodiment of the treatment head, as shown in FIG. 3, the treatment head 10 may be mounted on an annular roller, and the annular roller has a central opening in which the target region is disposed. Of course, the treatment head may be mounted on the C-arm, etc., and may be any existing method, which is not limited in the present application. The embodiment of the present application is exemplified by taking the treatment head mounted on the annular roller as an example.

Figure 5:
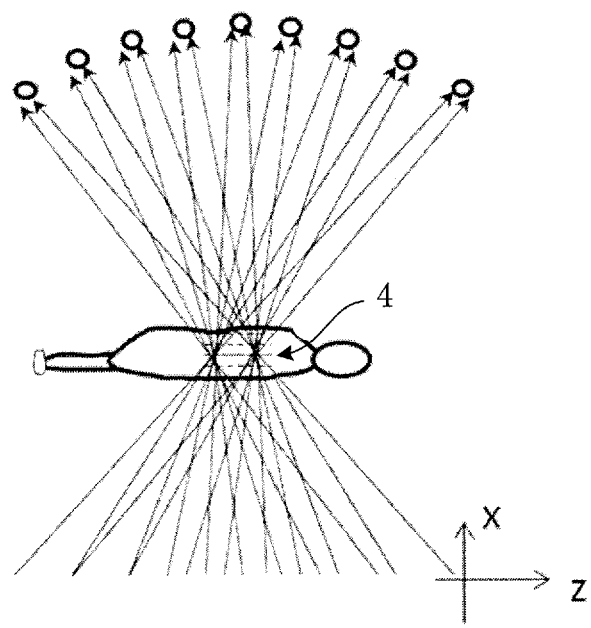
FIG. 5 is a schematic diagram of back projection calculation according to embodiments of the present disclosure.
Figure 7:
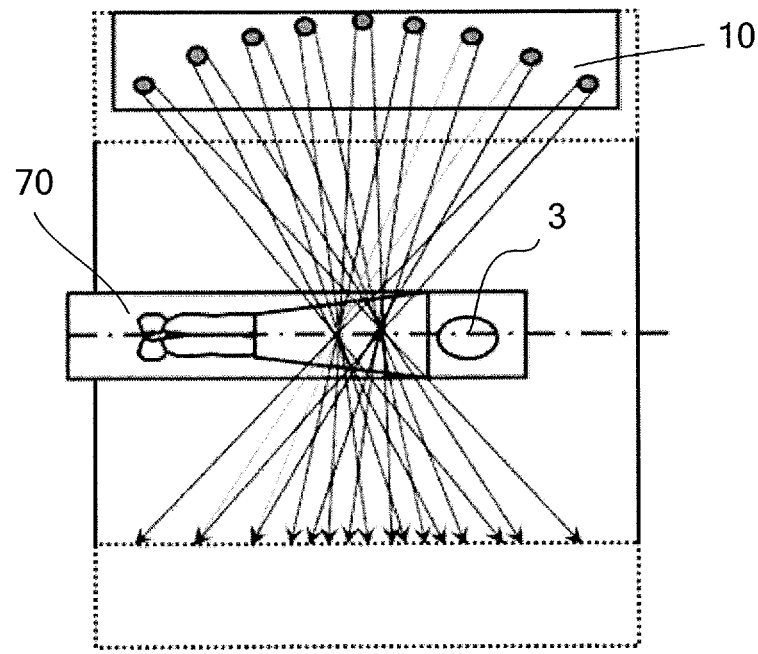
FIG. 7 is schematic diagram illustrating that a radiation source according to embodiments of the present disclosure emits a beam at an incident angle of beta.
Figure 8:
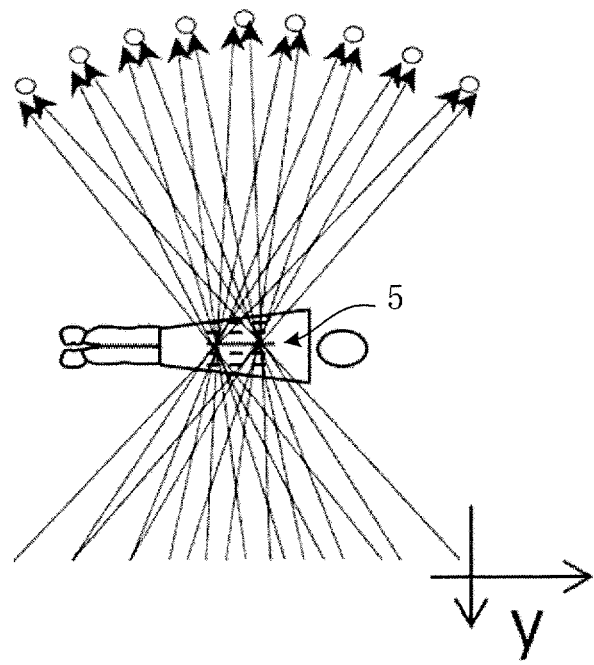
FIG. 8 is a schematic diagram of back projection calculation according to embodiments of the present disclosure.

The beam detector 20 is a device for converting the energy of the radiation beam into an electrical signal. As shown in FIG. 4 and FIG. 7, when the radiation beam passes through the human body, the detection unit on the beam detector (e.g. a photoelectric conversion unit) detects the radiation beam and converts the energy of the radiation beam into an electrical signal. The signal conversion unit in the beam detector 20 can process the electrical signal to acquire projection data. As shown in FIG. 5 and FIG. 8, an image of a tomographic plane acquired from reconstructing the projection data through a algorithm is the slice image.

Figure 9:
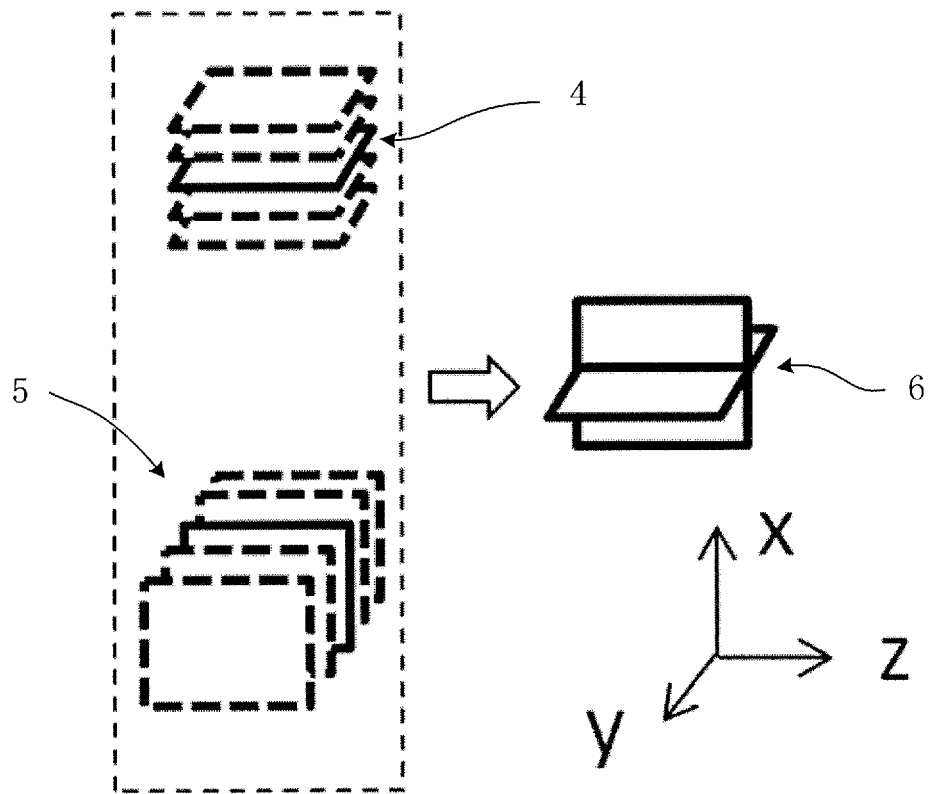
FIG. 9 is a schematic diagram of three-dimensional reconstruction based on slice projection data according to embodiments of the present disclosure.

In the present embodiment, the processor 30 can construct an image of the lesion in the target region according to the slice image. Exemplary, as shown in FIG. 9, the beam detector 20 receives radiation beams emitted by multiple radiation sources to generate a plurality of slice images. As shown in FIG. 9, taking an example in which multiple first slice images 4 are generated by the radiation source located at the first position and multiple second slice images 5 are generated by the radiation source located at the second position, the first slice image 4 and the second slice images 5 each includes multiple slice sub-images, the slice sub-images contain imaging information of the lesion, and the multiple slice sub-images can be processed to generate a three-dimensional image of the lesion through reconstruction.

In the radiation therapy apparatus of the present disclosure, the multiple radiation sources on the treatment head are distributed on a side of the target region at a preset angle, and the radiation beams emitted from the multiple radiation sources intersect. When the multiple radiation sources simultaneously emit radiation beams from different angles and pass through the lesion located in the target region, a slice image of the lesion can be generated by the beam detector. An image processing apparatus can generate a three-dimensional image of the lesion based on the slice image. For example, when five radiation sources are placed on the treatment head 10 at −10°, −5°, 0°, 5°, and 10° respectively, the treatment head turns on all the radiation sources at an alfa angle. Each radiation source forms a projection datum on the beam detector and generates a first slice sub-image, each first slice sub-image being perpendicular to the viewing angle of alfa to form a 3D slice image layer. Of course, only one of the radiation sources may be used to emit a radiation beam in use. A 2D image of the lesion can be acquired through the back projection reconstruction algorithm. According to the acquired 2D image of the lesion, the lesion can be positioned initially, and preliminary therapy information can be provided. For multiple radiation sources, since multiple radiation sources are irradiated from multiple angles in one irradiation, multiple projection data can be acquired in one process. Multiple projection data can generate multiple slice sub-images arranged spatially in a 3D form, and a three-dimensional image of the lesion can be generated according to the multiple slice sub-images. Therefore, the radiation therapy apparatus of the present disclosure can implement a three-dimensional imaging process in real time, so that the tumor can be tracked in real time without using an X-ray image processing system in a beam therapy operation. The tumor can be directly tracked by the treatment head of the beam therapy apparatus, and the human body can be positioned according to the reconstructed three-dimensional image before an operation. The imaging system can image in a short period of time without rotating the treatment head (because projection data from multiple perspectives can be acquired in one irradiation). The projection data are sufficient for three-dimensional reconstruction of the lesion. Therefore, this avoids displacement of the projection data as far as possible caused by even a micro movement of the human body, and improves the precision of imaging. Besides, the data can be used in the beam therapy apparatus. Imaging by directly using the beam of the treatment head eliminates the need for an imaging device and reduces the cost of the device.

Figure 2:
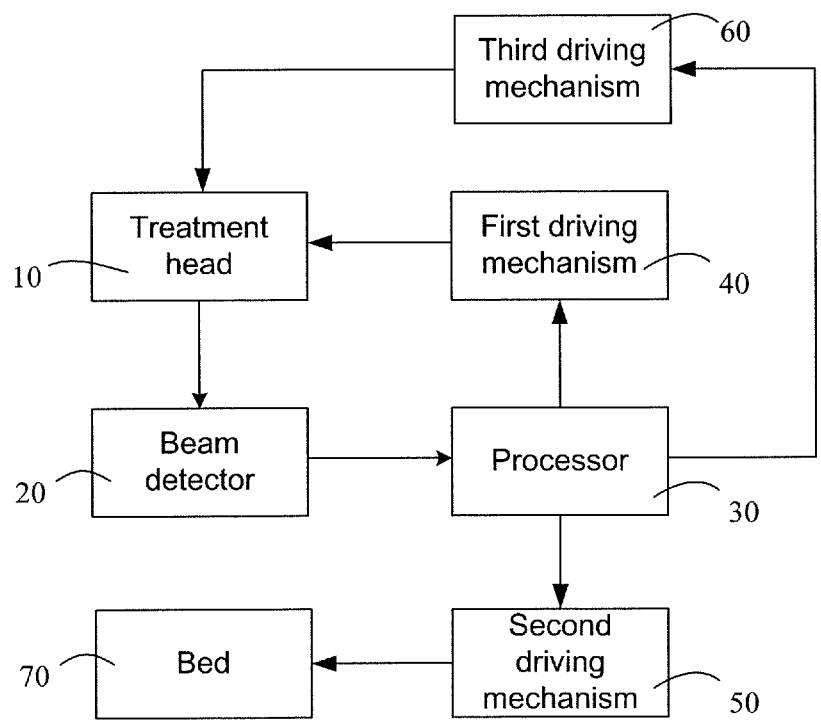
FIG. 2 is a schematic structural diagram of another radiation therapy apparatus according to example 1 of the present disclosure.

In the present embodiment, as shown in FIG. 2, a first driving mechanism for rotating the treatment head 10 is further included. The treatment head 10 can be rotated from a first position to a second position by the driving mechanism. The beam detector 20 can be rotated following the rotation of the treatment head. Alternatively, beam detectors are also disposed at the first position and the second position respectively, so that the beam detector can receive radiation beams emitted from the treatment head at both the first position and the second position.

Figure 6:
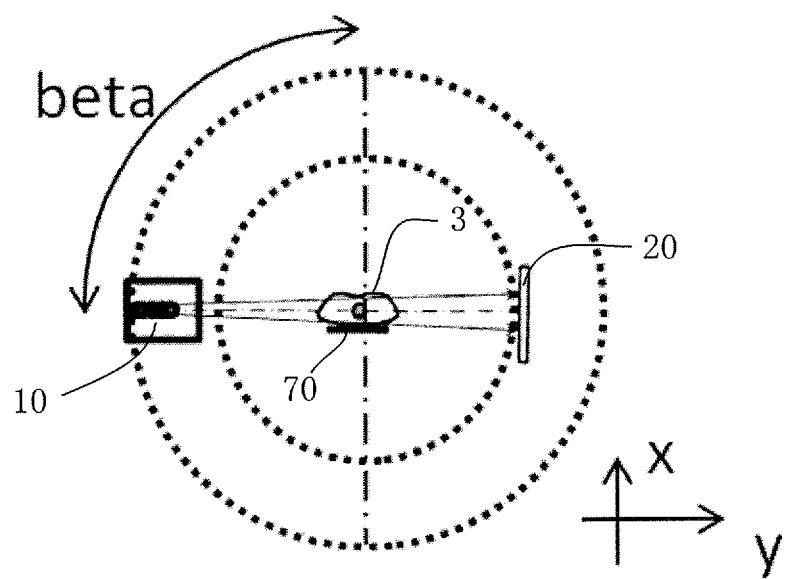
FIG. 6 is a schematic diagram illustrating that a radiation source according to embodiments of the present disclosure rotates to an incident angle of beta.

Exemplarily, as shown in FIG. 6, the first driving mechanism may be a cylinder with a central opening, the patient is located at the central opening of the cylinder, and the cylinder rotates around a central axis to drive the treatment head to rotate from a first position (alfa) to a second position (beta). That is, the treatment head is rotated from the first position to the second position by 90°, so that a three-dimensional image of the tumor can be acquired. The projection data includes first projection data acquired by the beam detector when the treatment head is at the first position, and second projection data acquired by the beam detector when the treatment head is at the second position. For example, when the treatment head is at the first position, the acquired first slice image is substantially perpendicular to the x-axis, and when the treatment head is rotated by 90° to the second position, the acquired second slice image is substantially perpendicular to the y-axis. Therefore, the intersection angle between the acquired two sets of slice images is 90°. The intersecting slice images contain more information of three-dimensional space, and the three-dimensional images of the lesion reconstructed by using the two sets of intersecting slice images are more accurate.

In the present embodiment, the treatment head includes at least an arched surface or a hemispherical surface such that the multiple radiation sources can be distributed at a preset angle and the radiation beams of the multiple radiation sources intersect with each other. Of course, any two of the multiple sources have a preset angle. It is also possible that the treatment head comprises at least two radiation sources in the axial direction. The specific arrangement of the radiation source is not specifically limited in the present application, and only the above is exemplified.

In an embodiment of the present disclosure, the radiation therapy apparatus further includes a pivoting mechanism for driving the treatment head to pivot about an axis. Exemplarily, the treatment head may be connected to the cylinder through a connecting shaft, and the connecting shaft may be connected with a joinball; the joinball drives the treatment head to rotate in different planes, thereby enabling pivoting of the treatment head. Certainly, there are many ways for the treatment head to pivot. The implementation manners of the treatment head are not limited in the embodiments of the present disclosure, and the above pivoting manner is merely taken as an example to facilitate the description.

As shown in FIG. 2 and FIG. 3, the therapy apparatus further includes a bed 70 and a second driving mechanism for driving the bed 70. The bed 70 is movable in an irradiation direction of the radiation beam. The distance between the bed 70 and the treatment head 10 affects the size of the region through which the radiation beam passes over the lesion. When the lesion of the human body needs to be integrally imaged, the second driving mechanism can move the bed away from the treatment head. That is, the distance between the bed and the treatment head is increased, thereby increasing the area irradiated onto the human body by the radiation beam, and imaging a larger area of the tumor.

Further, the second driving mechanism can also drive the bed 70 to move three-dimensionally or six-dimensionally, e.g. move up and down, left and right, front and back, or rotationally. Thus, the position of the lesion can be adjusted to correspond to the target.

In the present embodiment, the adjustment of the target can be achieved by moving the treatment head or the bed, wherein the target is a region in the treatment plan that receives a high dose of radiation beam. Therefore, the lesion should be in the target to achieve a better therapeutic effect. The processor determines the position of the lesion according to the two-dimensional image or the three-dimensional image of the lesion generated in the present embodiment. The second driving mechanism drives the bed to move according to the determined position of the lesion, so as to move the lesion of the human body into the target.

Alternatively, in the present embodiment, the treatment head 10 is further provided with a third driving mechanism. The third driving mechanism can drive the treatment head to move according to the determined position of the lesion to adjust the target, so that the target is moved to the lesion region and the lesion is placed in the target. Taking a spherical treatment head as an example, it is moved mainly under the guidance of a curved guide rail. Therefore, the target is mainly adjusted by rotating the treatment head via the curved guide rail, so that the position of the radiation source is changed, thereby forming a non-coplane with the rotation of the roller to adjust the position of the target. Taking a treatment head of a roller structure as another example, a motor drives the entire roller to rotate. The treatment head can also move along the curved guide rail or the like. The projection of the radiation source in the target is changed during rotation of the roller. Thereby the dose and shape of the target is adjusted.

In the present embodiment, the detector periodically receives a radiation beam according to a preset time or the detector continuously receives the radiation beam and filters the radiation beam. The following examples are exemplified by the detector periodically receiving the radiation beam according to a preset time. The processor acquires a reference position of the lesion, wherein the reference position may be a position where the lesion is acquired from the treatment plan or a position of the lesion determined by the radiation beam emitted previous time. The processor compares the acquired reference position of the lesion with the determined position of the lesion. If the comparison result indicates that the reference position of the lesion does not overlap the determined position of the lesion, the third driving mechanism will drive the treatment head to move according to the comparison result of the processor, such that the reference position of the lesion moves and overlaps the determined position of the lesion.

If the reference position is selected as an acquired position of the lesion in the treatment plan, the position of the lesion may be confirmed before the treatment, that is, the position before the treatment is determined. If the reference position is selected as a position of the lesion during the treatment determined by the radiation beam emitted previous time, the position of the lesion may be confirmed during the treatment. That is, tracking of the tumor in the treatment is achieved, so that the tumor is located in the target during the treatment process, thereby achieving precise treatment and improving the therapeutic effect.

In the present embodiment, the processor is further configured to acquire a motion signal of the human body, and determine a weight of the motion signal of the human body and a weight of the comparison result. In a case where the weight of the motion signal of the human body is greater than the weight of the comparison result, the second driving mechanism is further configured to drive the bed to move according to the motion signal of the human body; in a case where the weight of the motion signal of the human body is less than the weight of the comparison result, the second driving mechanism is further configured to drive the bed to move according to the comparison result. That is, the position of the lesion is adjusted by driving the bed so that the lesion is located in the target.

Specifically, a preset weight relationship may be stored in the processor, wherein the weight is a reliability weight of the motion signal to the comparison result. For example, because the tumor movement changes little during a last period of a respiratory signal, the weight of the motion signal of the human body is greater than the weight of the comparison result; and because the tumor movement changes greatly during an initial period of the respiratory signal, the weight of the motion signal of the human body is less than the weight of the comparison result. Of course, the last period or the initial period can be determined based on the actual respiratory cycle.

Alternatively, in the present embodiment, the processor is further configured to acquire a motion signal of the human body, and determine a weight of the motion signal of the human body and a weight of the comparison result; in a case where the weight of the motion signal of the human body is greater than the weight of the comparison result, the third driving mechanism is further configured to drive the treatment head to move according to the motion signal of the human body; in a case where the weight of the motion signal of the human body is less than the weight of the comparison result, the third driving mechanism is further configured to drive the treatment head to move according to the comparison result. That is, the position of the target is adjusted by driving the treatment head such that the lesion is located within the target.

In the present embodiment, during the treatment, when the treatment head periodically emits a radiation beam according to a preset time, the processor is further configured to acquire a reference position of the lesion, and compare the acquired reference position of the lesion with the determined position of the lesion. The reference position of the lesion is a position of the lesion in the treatment plan or a position of the lesion determined by the radiation beam emitted from the treatment head previous time; the treatment head is also used to adjust the beam intensity based on the comparison result of the processor. The processor is further configured to acquire a motion signal of the human body and determine a weight of the motion signal of the human body and a weight of the comparison result; in a case where the weight of the motion signal of the human body is greater than the weight of the comparison result, the treatment head is also used to adjust the beam intensity according to the motion signal of the human body; in a case where the weight of the motion signal of the human body is less than the weight of the comparison result, the treatment head is also used to adjust the beam intensity according to the comparison result so that the tumor can be tracked in real time during the treatment.

Exemplarily, the beam intensity may be adjusted as follows according to the comparison result: when the tumor is located in the target, the treatment head emits a dose based on the treatment plan to irradiate the tumor; when the tumor is partially located in the target, the treatment head emits a small dose to irradiate the tumor; when the tumor is completely out of the target, the treatment head may not emit a dose. That is, the treatment head may be turned off to stop it from emitting a therapeutic beam, thereby protecting normal tissues and preventing the normal tissues around the tumor from being excessively irradiated.

Example 2

Figure 10:
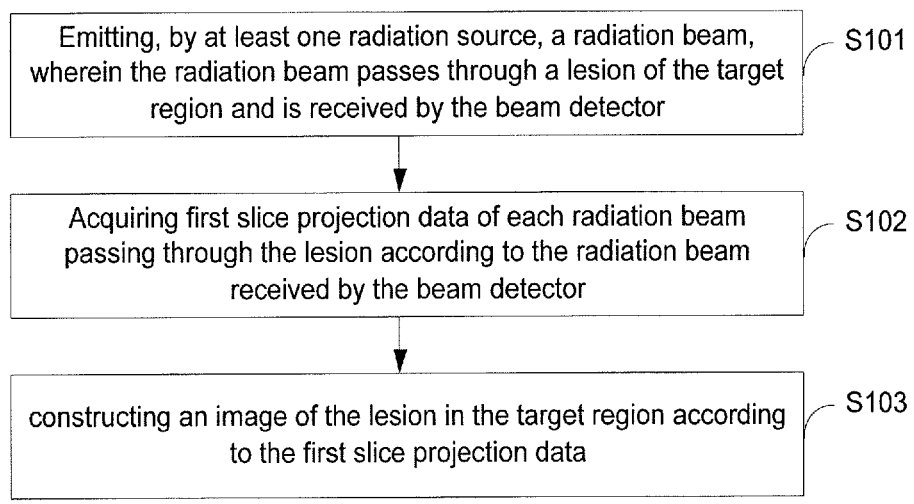
FIG. 10 is a schematic diagram of an imaging method according to embodiments of the present disclosure.

The present embodiment provides a beam imaging method applied to the radiation therapy apparatus. As shown in FIG. 1, the radiation therapy apparatus includes a treatment head 10 and a beam detector 20, wherein the treatment head 10 includes multiple radiation sources, and the multiple radiation sources (at least two radiation sources) are distributed on a side of the target region, wherein the multiple radiation beams emitted by the multiple radiation sources intersect in the target region, and a lesion is located in the target region; as shown in FIG. 10, the imaging method includes:

Step 101: Emitting, by at least one radiation source, a radiation beam, wherein the radiation beam passes through a lesion of the target region and is received by the beam detector.

Exemplary, a first position may be the alfa position as shown in FIG. 3. The target region is an area where the human lesion is located and through which the radiation beam of the radiation source passes, wherein the position of the human lesion is a part of the human body where the lesion occurs. As shown in FIG. 4, FIG. 5, FIG. 7 and FIG. 8, taking an example in which the radiation sources are arranged in the treatment head 10 in a shape of a spherical surface, the beams emitted from the radiation sources pass through the target region and the position of the lesion of the human body from one side. Merely one of the multiple radiation sources on the treatment head 10 may be turned on, that is, one radiation source emits a radiation beam and passes through the lesion, or multiple or all of the radiation sources may be simultaneously turned on, so that the radiation beams emitted from the radiation sources can pass through the lesion. If more radiation beams pass through the human lesion, more data about the lesion will be acquired. Of course, in practical applications, it is necessary to select an appropriate number of radiation sources depending on the size of the lesion.

Step 102: Acquiring first slice projection data of each radiation beam passing through the lesion according to the radiation beam received by the beam detector.

The first slice projection data includes lesion image information when the treatment head is at the first position. Specifically, referring to FIG. 4, when the radiation beam passes through the human body, a detection unit (such as a photoelectric conversion unit) on the beam detector detects the radiation beam and converts the energy of the radiation beam into an electrical signal. The signal conversion unit in the beam detector 20 can process the electrical signal to obtain projection data. As shown in FIG. 5, an image of a tomographic plane acquired from reconstructing the projection data through a "back projection reconstruction algorithm" is the slice image. Specifically, step 102 may be completed by a processor.

Step 103: constructing an image of the lesion in the target region according to the first slice projection data.

In the present embodiment, the processor 30 can construct an image of the lesion in the target region according to the slice image. Exemplarily, as shown in FIG. 9, the beam detector 20 receives radiation beams emitted from the multiple radiation sources to generate a plurality of slice images. As shown in FIG. 9, taking an example in which multiple first slice images 4 are generated by the radiation source located at the first position and multiple second slice images 5 are generated by the radiation source located at the second position, the first slice image 4 and the second slice images 5 each includes multiple slice sub-images, the slice sub-images contain imaging information of the lesion, and the multiple slice sub-images can be processed to generate a three-dimensional image of the lesion through reconstruction. When the radiation source is emitted from the first position where the radiation source is located, the detector may perform image processing according to the multiple first slice images 4 to produce a three-dimensional image of the lesion.

In the beam imaging method provided in the embodiments of the present disclosure, the multiple radiation sources on the treatment head are distributed on a side of the target region at a preset angle, and the radiation beams emitted by the multiple radiation sources intersect. When the multiple radiation sources simultaneously emit radiation beams from different angles and pass through a lesion located in the target region, a slice image of the lesion can be generated by the beam detector, and the image processing apparatus can generate a three-dimensional image of the lesion according to the slice image. For example, when five radiation sources are placed on the treatment head 10 at −10°, −5°, 0°, 5°, and 10° respectively, the treatment head turns on all of the radiation sources at an angle of alfa. Each radiation source forms a projection datum on the beam detector and generates a slice sub-image, each slice sub-image being perpendicular to the viewing angle of alfa to form a 3D slice image layer. Of course, only one of the radiation sources may be used to emit a radiation beam in use. A 2D image of the lesion can be acquired through the back projection reconstruction algorithm. According to the acquired 2D image of the lesion, the lesion can be positioned initially, and preliminary therapy information can be provided. For multiple radiation sources, since multiple radiation sources are irradiated from multiple angles in one irradiation, multiple projection data can be acquired in one process. Multiple projection data can generate multiple slice sub-images arranged spatially in a 3D form, and a three-dimensional image of the lesion can be generated according to the multiple slice sub-images. Therefore, the radiation therapy apparatus of the present disclosure can implement a three-dimensional imaging process in real time, so that the tumor can be tracked in real time without using an X-ray image processing system in a beam therapy operation. The tumor can be directly tracked by the treatment head of the beam therapy apparatus, and the human body can be positioned according to the reconstructed three-dimensional image before an operation. The imaging system can image in a short period of time without rotating the treatment head (because projection data from multiple perspectives can be acquired in one irradiation). The projection data are sufficient for three-dimensional reconstruction of the lesion. Therefore, this avoids displacement of the projection data as far as possible caused by even a micro movement of the human body, and improves the precision of imaging. Besides, the data can be used in the beam therapy apparatus. Imaging by directly using the beam of the treatment head eliminates the need for an imaging device and reduces the cost of the device.

Figure 11:
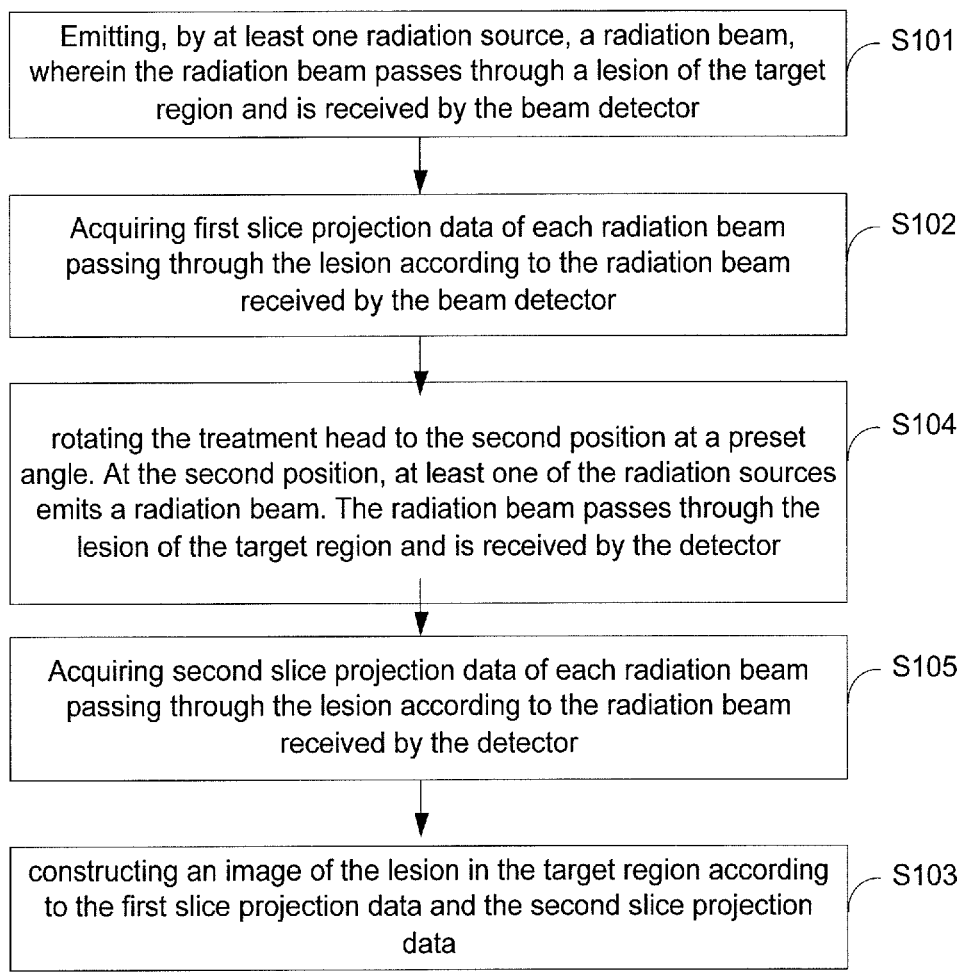
FIG. 11 is a schematic diagram of another imaging method according to embodiments of the present disclosure.

In the present embodiment, as shown in FIG. 11, the method further includes:

Step 104: rotating the treatment head to the second position at a preset angle. At the second position, at least one of the radiation sources emits a radiation beam. The radiation beam passes through the lesion of the target region and is received by the detector.

The preset angle may be set in the system in advance, wherein the preset angle may be, for example, 45°, 60°, etc. Of course, in the present embodiment, the preset angle is 90°, so that the first slice projection data and the second slice projection data perpendicular to each other may maximally include three-dimensional spatial information. Thereby a real image close to the lesion can be constructed.

In embodiments of the present disclosure, as shown in FIG. 3, the first position may be an alfa position; as shown in FIG. 6, the second position may be a beta position. That is, the treatment head is rotated from the first position to the second position by 90°. Thus, even if only one radiation source is used to emit a radiation beam, a three-dimensional image of the tumor can be acquired from the two perpendicular planes, as shown in FIG. 9.

Specifically, as shown in FIG. 2, the radiation therapy apparatus further includes a first driving mechanism for driving the treatment head 10 to rotate. The treatment head can be rotated from the first position to the second position by using the driving mechanism. The beam detector 20 can rotate following the treatment head. Alternatively, beam detectors are also arranged at the first position and the second position, so that they can receive radiation beams emitted by the treatment head at both the first position and the second position. The first driving mechanism shown in FIG. 6 can be a roller with a central opening. The patient is located at the central opening of the roller, and the roller revolves around the central axis to rotate the treatment head from the first position to the second position.

Step 105: Acquiring second slice projection data of each radiation beam passing through the lesion according to the radiation beam received by the detector, wherein the second slice projection data includes lesion information of the treatment head located at the second position.

Specifically, referring to FIG. 7, when the radiation beam passes through the human body, a detection unit (such as a photoelectric conversion unit) on the beam detector detects the radiation beam and converts the energy of the radiation beam into an electrical signal. The signal conversion unit in the beam detector 20 can process the electrical signal to acquire projection data. As shown in FIG. 8, an image of a tomographic plane acquired from reconstructing the projection data through a "back projection reconstruction algorithm" is the slice image. Specifically, step 105 may be completed by a processor.

The step 103 is as follows: constructing an image of the lesion in the target region according to the first slice projection data and the second slice projection data.

Referring to FIG. 9, the beam detector 20 receives radiation beams emitted by the multiple radiation sources from directions alfa and beta respectively and generates a plurality of slice sub-images. Radiation beams emitted by the radiation sources from alfa are received by the detector to generate a first slice image 4, wherein the first slice image 4 includes multiple first slice sub-images, and the first slice sub-image includes multiple flat image information of the lesion when the treatment head is located at the first position. Radiation beams emitted by the radiation sources from beta are received by the detector to generate a second slice image 5, wherein the second slice image 5 includes multiple second slice sub-images, and the second slice sub-image includes multiple image information of the lesion when the treatment head is located at the second position. According to the first slice image 4 and the second slice image 5, a three-dimensional image 6 of the lesion is reconstructed after image processing.

In the present embodiment, the therapy apparatus further includes a bed. Before a three-dimensional image of the lesion in the target region is constructed according to the slice image, the method further includes moving the bed to adjust the distance between the bed and the treatment head, thereby adjusting the size of the region where the radiation beam passes through the human body. Based on this, the lesion can be better pinpointed in the target. As shown in FIG. 2, the therapy apparatus further includes a bed 70 and a second driving mechanism 50 for driving the bed 70, the bed 70 being movable in a direction of irradiation of the radiation beam. The distance between the bed and the treatment head affects the size of the area through which the radiation beam passes over the lesion. When the lesion of the human body needs to be integrally imaged, the bed can be moved away from the treatment head by the second driving mechanism. That is, the distance between the bed and the treatment head is increased, thereby increasing the area irradiated onto the human body by the radiation beam, and imaging a larger area of the tumor. Further, the second driving mechanism can also drive the bed 70 to move three-dimensionally or six-dimensionally. Three-dimensional or six-dimensional movement of the bed 70 enables adjustment of the position of the lesion or adjustment of the target.

In the present embodiment, the method further includes: determining a position of the lesion according to the constructed three-dimensional image, and adjusting a position of the lesion of the target region and/or a position of the target according to the position of the lesion, so that the lesion of the target region is located in the target of the treatment plan. The target is an area where large doses of radiation beams are received, and disposing the lesion in the target can improve the effectiveness of the treatment. For example, as shown in FIG. 2, the treatment apparatus can further include a bed 70 and a second driving mechanism for driving the bed 70, the bed 70 being movable in the direction of irradiation of the radiation beam. The distance between the bed and the treatment head affects the size of the area through which the radiation beam passes over the lesion. When the lesion of the human body needs to be integrally imaged, the second driving mechanism can move the bed away from the treatment head, that is, increase the distance between the bed and the treatment head. Further, the second driving mechanism can also drive the bed 70 to move three-dimensionally or six-dimensionally, and three-dimensional or six-dimensional movement of the bed 70 enables adjustment of the position of the lesion in the target region. For example, adjustment of the target can be achieved by moving the treatment head 10 or the bed 70. The processor determines the position of the lesion based on the constructed three-dimensional image of the lesion, and the second driving mechanism drives the bed to move according to the determined position of the lesion such that the lesion of the human body (i.e., the lesion in the target region) can be moved into the target. Alternatively, in the present embodiment, the treatment head 10 is further provided with a third driving mechanism. The third driving mechanism can drive the treatment head to move according to the determined position of the lesion, so as to adjust the target. Thereby, the target is moved to the lesion region and the lesion is disposed in the target. Taking a spherical treatment head as an example, the treatment head is mainly moved under guidance of a curved guide rail. Therefore, the target is mainly adjusted by rotating the treatment head via the curved guide rail, so that the position of the radiation source is changed, thereby forming a non-coplane with the rotation of the roller to adjust the position of the target. Taking a treatment head of a roller structure as another example, a motor drives the entire roller to rotate. The treatment head can also move along the curved guide rail or the like. The projection of the radiation source in the target is changed during rotation of the roller. Thereby the dose and shape of the target is adjusted.

Figure 12:
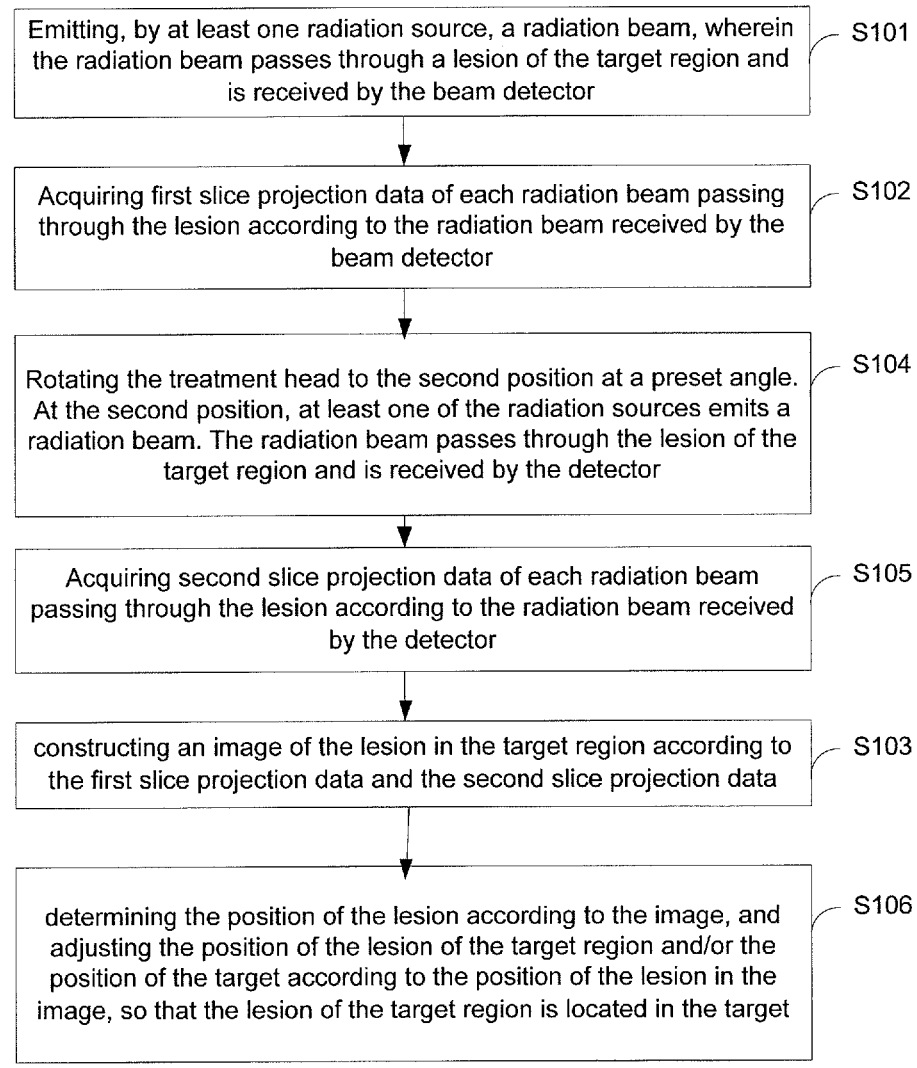
FIG. 12 is a schematic diagram of still another imaging method according to embodiments of the present disclosure.

As shown in FIG. 12, the method further includes:

Step 106: determining the position of the lesion according to the image, and adjusting the position of the lesion of the target region and/or the position of the target according to the position of the lesion in the image, so that the lesion of the target region is located in the target.

Specifically, step 106 may be positioning the patient before treatment: acquiring the position of the lesion in the treatment plan, comparing the position of the lesion determined from the image with the position of the lesion in the treatment plan, and adjusting the position of the lesion in target region and/or the position of the target in a case where the position of the lesion does not match the position of the lesion in the treatment plan, such that the lesion in the target region is located in the target, thereby completing the positioning before treatment.

Figure 13:
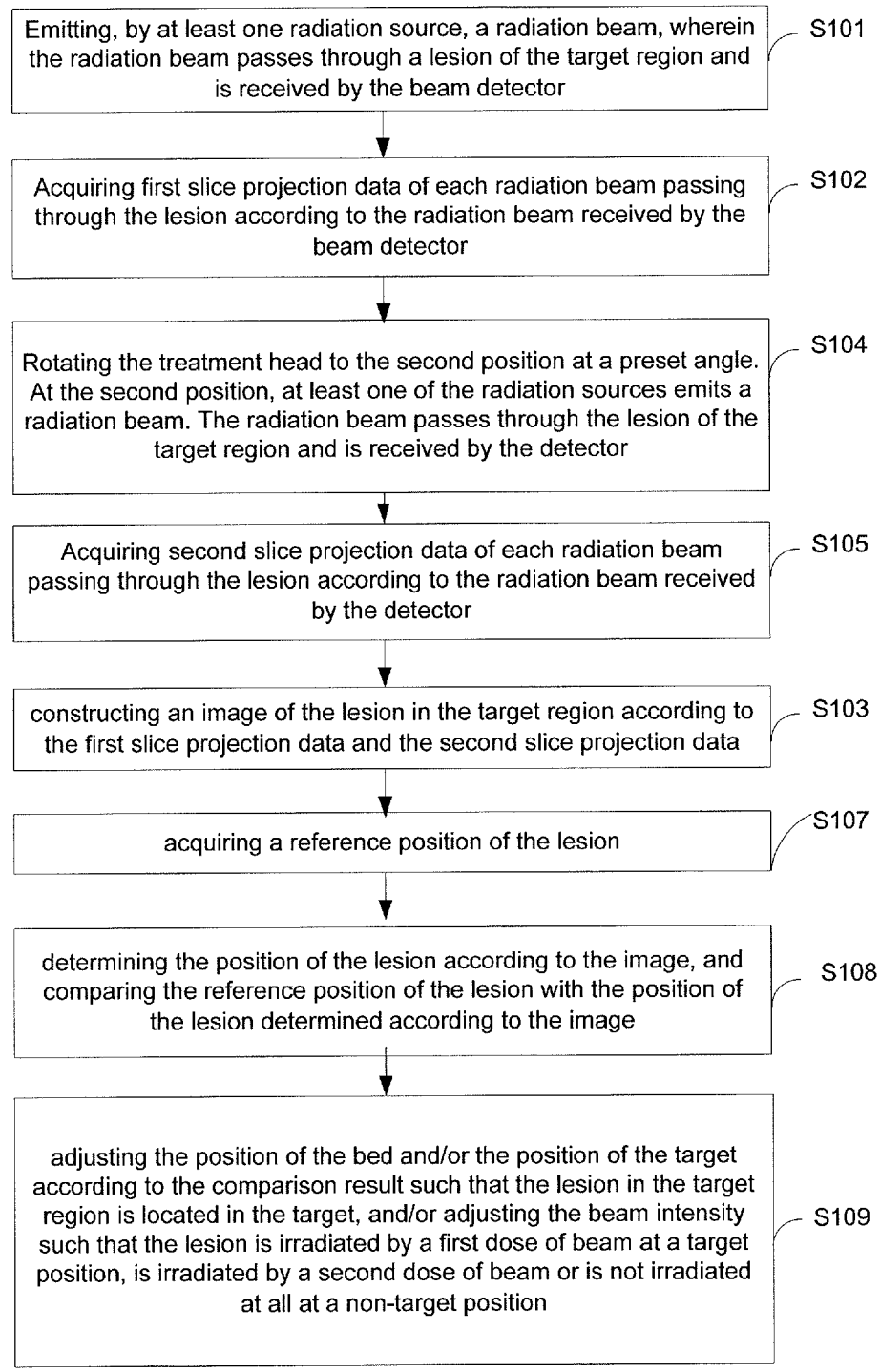
FIG. 13 is a schematic diagram of yet still another imaging method according to embodiments of the present disclosure.

Alternatively, in the beam imaging method according to embodiments of the present disclosure, the lesion can also be tracked during the treatment. As shown in FIG. 13, the beam imaging method includes:

Step 107: acquiring a reference position of the lesion. The reference position of the lesion may be a position of the lesion determined in the treatment plan, or a position of the lesion determined according to the image constructed during the irradiation by the previous radiation beam.

Step 108: determining the position of the lesion according to the image, and comparing the reference position of the lesion with the position of the lesion determined according to the image.

Step 109, adjusting the position of the bed and/or the position of the target according to the comparison result such that the lesion in the target region is located in the target, and/or adjusting the beam intensity such that the lesion is irradiated by a first dose of beam at a target position, is irradiated by a second dose of beam or is not irradiated at all at a non-target position.

Specifically, the bed may be adjusted according to the comparison result such that the lesion of the target region is located in the target. Alternatively, the position of the target may be adjusted according to the comparison result such that the lesion of the target region is located in the target. Alternatively, positions of the target and the bed may be adjusted according to the comparison result such that the lesion in the target region is located in the target. Alternatively, the bed or the beam intensity may be adjusted according to the comparison result such that the lesion is irradiated by a first dose of beam at a target position, is irradiated by a second dose of beam or is not irradiated at all at a non-target position. Alternatively, the bed and the beam intensity may be adjusted according to the comparison result such that the lesion is irradiated by a first dose of beam at a target position, is irradiated by a second dose of beam or is not irradiated at all at a non-target position. Alternatively, the position of the target and the beam intensity may be adjusted according to the comparison result such that the lesion is irradiated by a first dose of beam at a target position, is irradiated by a second dose of beam or is not irradiated at all at a non-target position.

In order to improve the accuracy of treatment, while ensuring that the range of images is sufficient for the treatment needs, a part outside the target and the target will be irradiated simultaneously by radiation beams, although their doses are different. The target will be irradiated by a first dose of beam, and the non-target will be irradiated by a second dose of beam. Of course, the non-target may not be irradiated by a second dose of beam. In the present embodiment, the first dose is greater than the second dose.

According to the comparison result between the reference position and the position of the lesion according to the image constructed in the current irradiation, the position of the bed or the target can be adjusted in the above manner. Besides, the beam intensity is adjusted so that the lesion is irradiated by a first dose of beam at a target position, is irradiated by a second dose of beam or is not irradiated at all at a non-target position.

In the present embodiment, before adjusting the position of the bed according to the above comparison result, and/or adjusting the beam intensity, the method further includes: acquiring a motion signal of the human body, and determining a weight of the motion signal of the human body and a weight of comparison result. In a case where the weight of the motion signal of the human body is less than the weight of the comparison result, the second driving mechanism is further configured to drive the bed to move according to the comparison result; in a case where the weight of the motion signal of the human body is greater than the weight of the comparison result, the second driving mechanism is further configured to drive the bed to move according to the motion signal. The motion signal of the human body comes from subtle movements of the human body, such as heartbeat, breathing and tiny movement. The position of the lesion can be adjusted by driving the bed to move, thus disposing the lesion in the target. Alternatively, in a case where the weight of the motion signal of the human body is less than the weight of the comparison result, the third driving mechanism is further configured to drive the treatment head to move according to the comparison result; in a case where the weight of the motion signal of the human body is greater than the weight of the comparison result, the third driving mechanism is further configured to drive the treatment head to move according to the motion signal. The position of the target can be adjusted by driving the treatment head to move, thus disposing the lesion in the target.

Alternatively, the beam intensity is adjusted while adjusting the bed or treatment head, such that the lesion is irradiated by a first dose of beam at a target position, is irradiated by a second dose of beam or is not irradiated at all at a non-target position. The first dose is greater than the second dose, such that the first dose of beam can kill the lesion and the second dose of beam irradiates a smallest area to avoid damage to normal tissues.

Example 3

Figure 14:
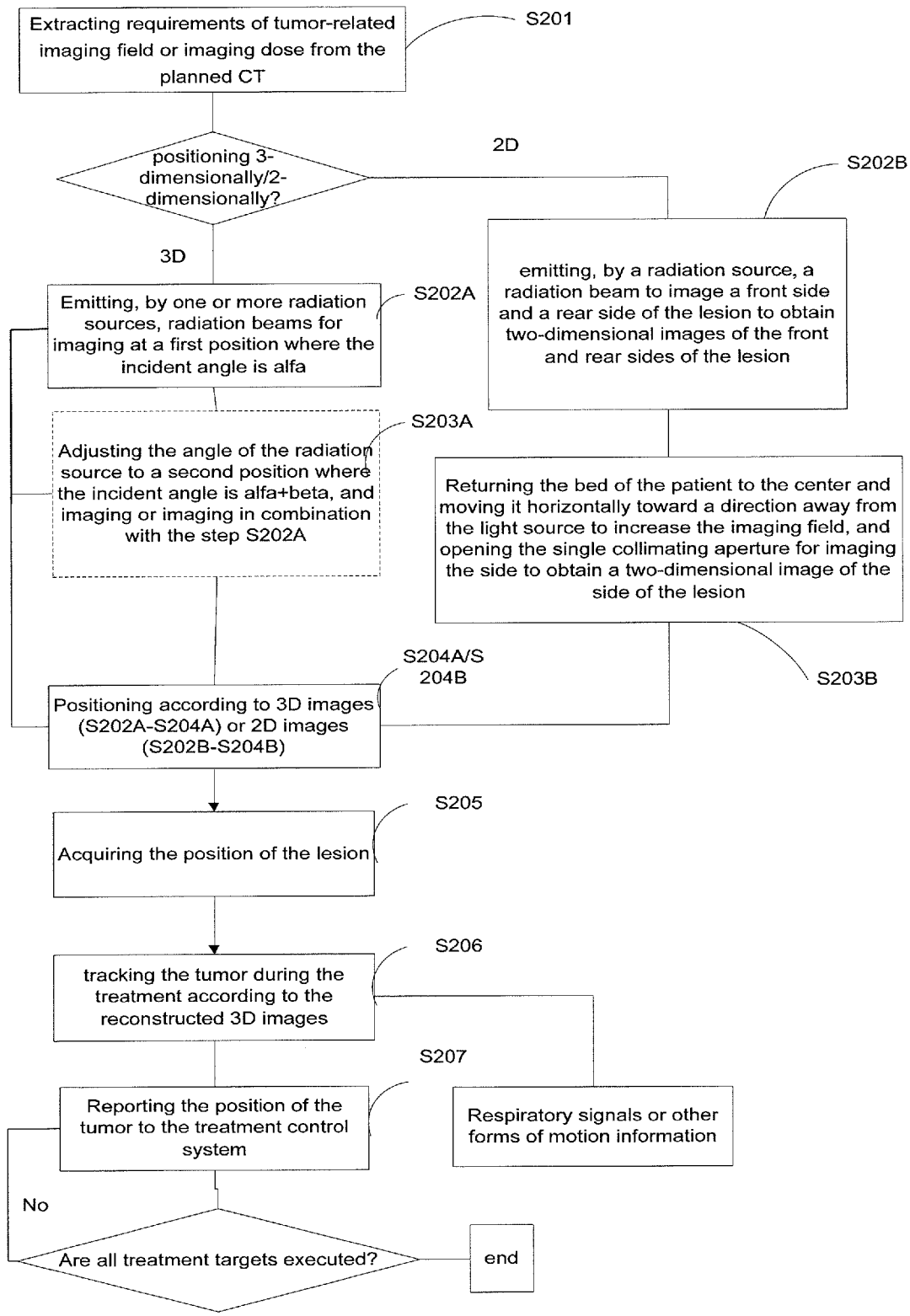
FIG. 14 is a schematic diagram of an application according to embodiments of the present disclosure.

A specific embodiment about positioning based on imaging and tracking a lesion (in the present embodiment, a tumor is taken as an example) based on imaging during the treatment is provided to further illustrate the present disclosure. As shown in FIG. 14, the process of using a radiation therapy apparatus for tumor treatment includes the steps of:

S201, extracting requirements of tumor-related imaging field or imaging dose from the planned CT.

Positioning the patient on the bed three-dimensionally or two-dimensionally, wherein positioning three-dimensionally is to move the patient three-dimensionally, and positioning two-dimensionally is to move the patient on a plane, e.g. to move the patient horizontally.

Positioning three-dimensionally includes the following steps:

S202A: Emitting, by one or more radiation sources, radiation beams for imaging at a first position where the incident angle is alfa, as shown in FIG. 3. The imaging process is the same as that in Example 2 described above. The radiation beam emitted by the radiation source on the treatment head passes through the human body, and the first projection data is acquired at the first position by the beam detector. By performing a back projection algorithm on the first projection data, multiple first slice images are acquired, and a three-dimensional image of the lesion is reconstructed according to the first slice image.

S203A: Adjusting the angle of the radiation source, as shown in FIG. 6, so that the radiation source is at the second position where the incident angle is beta. As shown in FIG. 9, at the second position where the incident angle is beta, one or more radiation sources emit radiation beams to form multiple second slice images 5. Thereby, three-dimensional imaging is performed in combination with the first slice image in step S202A and the second slice image in step S203A.

It will be noted that the three-dimensional reconstruction of the tumor can also be completed according to the first slice image acquired in step S202A or the second slice image acquired in step S203A. In order to reflect the tumor information accurately, after the patient is positioned, the patient is irradiated at an incident angle of beta (the second position) to obtain the second projection data and the second slice image. A three-dimensional image of the tumor is reconstructed according to the first slice image and the second slice image.

S204A: Positioning according to the acquired three-dimensional image (S202A-S203A). Specifically, the processor takes the position of the lesion acquired from the treatment plan as a reference position. The processor determines the position of the lesion according to the acquired three-dimensional image. The processor compares the acquired reference position of the lesion with the determined position of the lesion. If the comparison result indicates that the reference position of the lesion does not overlap the determined position of the lesion, the second driving mechanism drives the bed to move based on the comparison result of the processor such that the determined position of the lesion overlaps the reference position of the lesion. Alternatively, the third driving mechanism drives the treatment head to move according to the comparison result of the processor such that the reference position of the lesion moves and overlaps the determined position of the lesion. Alternatively, the second driving mechanism drives the bed to move according to the comparison result of the processor while the third driving mechanism drives the treatment head to move according to the comparison result of the processor such that the reference position of the lesion overlaps the determined position of the lesion.

Positioning two-dimensionally includes the following steps:

S202B: lowering the height of the bed of the patient to increase the area through which the radiation beam passes, and a radiation source emits a radiation beam to image a front side and a rear side of the lesion to obtain two-dimensional images of the front and rear sides of the lesion.

S203B: Returning the bed of the patient to the center and moving it horizontally toward a direction away from the light source to increase the imaging field, and opening the single collimating aperture for imaging the side to obtain a two-dimensional image of the side of the lesion.

S204B: Positioning according to the two-dimensional image of the lesion (S202B-S204B). Specifically, the position of the lesion acquired by the processor from the treatment plan is taken as a reference position. The processor determines the position of the lesion according to the obtained two-dimensional image. The processor compares the acquired reference position of the lesion with the determined position of the lesion. If the comparison result indicates that the reference position of the lesion does not overlap the determined position of the lesion, the second driving mechanism drives the bed to move according to the comparison result of the processor such that the determined position of the lesion overlaps the reference position of the lesion. Alternatively, the third driving mechanism drives the treatment head to move according to the comparison result of the processor to cause the reference position of the lesion to move and overlap the determined position of the lesion. Alternatively, the second driving mechanism drives the bed to move according to the comparison result of the processor while the third driving mechanism drives the treatment head to move according to the comparison result of the processor such that the reference position of the lesion overlaps the determined position of the lesion.

S205: Acquiring a position of the lesion during the treatment by referring to the images of the lesion in the above steps 202A-203A or the above steps 202B-203B.

Step 206: tracking the tumor during the treatment according to the reconstructed image.

Exemplarily, the method specifically includes the following steps: Step 2061: acquiring a reference position of the lesion. The reference position of the lesion is the position of the lesion determined according to the radiation beam of the previous cycle.

Step 2062, comparing the reference position of the lesion with the position of the lesion determined according to the images.

Step 2063: Acquiring a motion signal of the human body, and determining a weight of the motion signal of the human body and a weight of the comparison result.

In a case where the weight of the motion signal of the human body is less than the weight of the comparison result, the second driving mechanism is further configured to drive the bed to move according to the comparison result; in a case where the weight of the motion signal of the human body is less than the weight of the comparison result, the second driving mechanism is further configured to drive the bed to move according to the motion signal. The motion signal of the human body comes from subtle movements of the human body, such as heartbeat, breathing and tiny movements. The position of the lesion can be adjusted by driving the bed to move, thereby disposing the lesion in the target.

S209: Reporting the position of the tumor to the treatment control system, and transmitting the tracking result of the tumor in step S206 to the treatment control system.

After the treatment control system confirms the therapeutic target, the treatment control system determines whether to perform a beam treatment process.

The above is a detailed description of the present invention in conjunction with the preferred embodiments, but it cannot be considered that specific implementation of the present disclosure is limited by the above description. A person of ordinary skill in the art may make several simple deductions or replacement without departing from the spirit of the present disclosure, which shall all be included in the protection scope of the present disclosure.

What is claimed is:

1. A radiation therapy apparatus, comprising:
   a treatment head, wherein the treatment head comprises multiple radiation sources, the multiple radiation sources are distributed on a side of a target region, radiation beams emitted by at least two of the multiple radiation sources intersect in the target region;
   a beam detector configured to receive the radiation beams passing through a lesion and simultaneously emitted by the at least two of the multiple radiation sources to acquire projection data of the radiation beams passing through the lesion, and generate a slice image of the lesion according to the acquired projection data, wherein the beam detector periodically receives a radiation beam or continuously receives a radiation beam according to a preset time; the slice image includes multiple sub-slice images parallel to each other;
   a processor configured to construct an image of the lesion in the target region according to the multiple sub-slice images generated by the beam detector, determine a position of the lesion according to the image of the lesion, acquire a reference position of the lesion, and compare the acquired reference position of the lesion with the determined position of the lesion; and the processor further configured to acquire a motion signal of a human body and determine a weight of a comparison result and a weight of the motion signal of the human body, wherein the reference position of the lesion is a position of the lesion in a treatment plan, or a position of the lesion determined according to the radiation beam emitted by the treatment head previous time;

a bed; and a second driving mechanism configured to drive the bed to move according to the comparison result determined by the processor, wherein in a case where the weight of the motion signal of the human body is less than the weight of the comparison result, the second driving mechanism is further configured to drive the bed and/or the treatment head to move according to the motion signal of the human body;

in a case where the weight of the motion signal of the human body is greater than the weight of the comparison result, the second driving mechanism is further configured to drive the bed and/or the treatment head to move according to the comparison result.

2. The radiation therapy apparatus according to claim 1, wherein the radiation therapy apparatus further comprises a first driving mechanism for driving the treatment head to rotate circumferentially.

3. The radiation therapy apparatus according to claim 2, wherein the first driving mechanism drives the treatment head to rotate, and the treatment head is located at different positions to emit a radiation beam;

the beam detector is further configured to receive a radiation beam emitted by the radiation source when the treatment head is at different positions to obtain a slice image of the same radiation source at different positions;

the processor is further configured to construct an image of the target region according to the sliced images at different locations.

4. The radiation therapy apparatus according to claim 1, wherein the radiation therapy apparatus further comprises a pivoting mechanism for driving the treatment head to pivot about an axis.

5. The radiation therapy apparatus according to claim 1, wherein the processor is further configured to determine a position of the target region according to the image of the lesion;

the radiation therapy apparatus further comprises a third driving mechanism configured to drive the treatment head to move, thereby adjusting a position of a target.

6. The radiation therapy apparatus according to claim 5, wherein the third driving mechanism is further configured to drive the treatment head to move according to the comparison result determined by the processor.

7. The radiation therapy apparatus according to claim 1, wherein among the multiple radiation sources, any two of the radiation sources have a preset angle.

8. The radiation therapy apparatus according to claim 1, wherein the treatment head includes at least two radiation sources in a circumferential direction.

9. A beam imaging method applied to a radiation therapy apparatus, the radiation therapy apparatus comprising a treatment head, a bed and a beam detector, wherein the treatment head comprises multiple radiation sources, the multiple radiation sources are distributed on one side of a target region, wherein multiple radiation beams emitted by at least two of the multiple radiation sources intersect in the target region, characterized in that the imaging method comprises:

emitting, by at least two of the radiation sources, radiation beams simultaneously;

receiving, by the beam detector, the radiation beams passing through the target region;

acquiring, by the beam detector, first slice projection data of the radiation beams passing through the target region, wherein the first slice projection data comprises lesion image information when the treatment head is at a first position, the first slice projection data includes sub-slice projection data corresponding to each of the radiation sources, a slice image is generated according to the first slice projection data, and the slice image includes multiple first sub-slice images parallel to each other;

constructing an image of the lesion in the target region based on the multiple first sub-slice images corresponding to the at least two radiation sources;

determining a position of the lesion according to the image;

adjusting the position of the lesion in the target region and/or the position of the target according to the position of the lesion in the image such that the lesion in the target region is located in the target;

acquiring a reference position of the lesion, wherein the reference position of the lesion is a position of the lesion in the treatment plan, or a position of the lesion determined according to the radiation beam emitted by the treatment head previous time;

comparing the reference position of the lesion with the position of the lesion determined according to the image;

the target region located in the target, and/or adjusting the beam intensity such that the lesion is irradiated by a first dose of beam at a target position, is irradiated by a second dose of beam or is not irradiated at all at a non-target position, wherein the first dose is greater than the second dose;

before a bed position is adjusted according to a comparison result and/or before the beam intensity is adjusted, the method further comprises: acquiring a motion signal of the human body;

determining a weight of the motion signal of the human body and a weight of the comparison result;

adjusting the position of the bed and/or the position of the target according to the comparison result, and/or adjusting the beam intensity in a case where the weight of the motion signal of the human body is less than the weight of the comparison result adjusting the position of the bed according to the motion signal, and/or, adjusting the beam intensity in a case where the weight of the motion signal of the human body is greater than the weight of the comparison result.

10. The beam imaging method according to claim 9, wherein the method further comprises: rotating the treatment head to a second position at a preset angle, emitting, by at least one of the radiation sources, a radiation beam at the second position; the beam detector receives a radiation beam passes through the target region r; acquiring a second slice projection data of the target region, wherein the second slice projection data comprises lesion image information when the treatment head is at the second position;

constructing an image of the lesion in the target region according to the second slice projection data or according to the first slice projection data and the second slice projection data.

11. The beam imaging method according to claim 10, wherein the preset angle is 90°.

12. The beam imaging method according to claim 9, further comprises: moving the bed to adjust a distance between the bed and the treatment head.

13. A radiation therapy apparatus, comprising:
a treatment head, wherein the treatment head comprises multiple radiation sources, the multiple radiation sources are distributed on a side of a target region, radiation beams emitted by at least two of the multiple radiation sources intersect in the target region;
a beam detector configured to receive the radiation beams passing through a lesion and simultaneously emitted by the at least two of the multiple radiation sources to acquire projection data of each the radiation beams passing through the lesion, and generate a slice image of the lesion according to the acquired projection data, wherein the beam detector periodically receives a radiation beam or continuously receives a radiation beam according to a preset time, the slice image includes multiple sub-slice images parallel to each other; and
a processor configured to construct an image of the lesion in the target region according to the multiple sub-slice images generated by the beam detector, acquire a reference position of the lesion and compare the acquired reference position of the lesion with the determined position of the lesion; the processor further configured to acquire a motion signal of a human body and determine a weight of a comparison result and a weight of the motion signal of the human body, wherein the reference position of the lesion is a position of the lesion in a treatment plan, or a position of the lesion determined according to the radiation beam emitted by the treatment head previous time; wherein
the treatment head is further configured to adjust a beam intensity according to the comparison result of the processor;
in a case where the weight of the motion signal of the human body is less than the weight of the comparison result, the treatment head is further configured to adjust the beam intensity according to the motion signal of the human body;
in a case where the weight of the motion signal of the human body is greater than the weight of the comparison result, the treatment head is further configured to adjust the beam intensity according to the comparison result.

* * * * *